(12) United States Patent
Yoshida et al.

(10) Patent No.: US 7,935,047 B2
(45) Date of Patent: May 3, 2011

(54) DOUBLE-BALLOON ENDOSCOPE SYSTEM

(75) Inventors: Takatoshi Yoshida, Hachioji (JP);
Sumihiro Uchimura, Sagamihara (JP);
Akira Taniguchi, Hachioji (JP)

(73) Assignee: Olympus Corporation, Tokyo (JP)

( * ) Notice: Subject to any disclaimer, the term of this patent is extended or adjusted under 35 U.S.C. 154(b) by 1261 days.

(21) Appl. No.: 11/523,290

(22) Filed: Sep. 19, 2006

(65) Prior Publication Data

US 2007/0049797 A1 Mar. 1, 2007

Related U.S. Application Data

(63) Continuation of application No. PCT/JP2005/004807, filed on Mar. 17, 2005.

(30) Foreign Application Priority Data

Mar. 19, 2004 (JP) ................................. 2004-081650

(51) Int. Cl.
*A61B 1/00* (2006.01)
(52) U.S. Cl. ......... 600/117; 600/115; 600/116; 600/118
(58) Field of Classification Search .................. 600/115, 600/116, 117, 118, 424
See application file for complete search history.

(56) References Cited

U.S. PATENT DOCUMENTS

| | | | |
|---|---|---|---|
| 4,690,131 A * | 9/1987 | Lyddy et al. ................... | 600/115 |
| 4,862,874 A * | 9/1989 | Kellner .......................... | 600/116 |
| 4,960,106 A * | 10/1990 | Kubokawa et al. ........... | 600/104 |
| 5,201,753 A * | 4/1993 | Lampropoulos et al. ...... | 606/192 |
| 6,007,482 A * | 12/1999 | Madni et al. ................... | 600/115 |
| 6,203,493 B1 * | 3/2001 | Ben-Haim ...................... | 600/117 |
| 2003/0055317 A1 * | 3/2003 | Taniguchi et al. ............. | 600/117 |
| 2004/0116775 A1 * | 6/2004 | Taniguchi et al. ............. | 600/117 |
| 2005/0137457 A1 * | 6/2005 | Machida ........................ | 600/115 |
| 2005/0222500 A1 * | 10/2005 | Itoi ................................ | 600/180 |
| 2007/0299308 A1 * | 12/2007 | Fujikura et al. ............... | 600/115 |

FOREIGN PATENT DOCUMENTS

| | | |
|---|---|---|
| JP | 08-107875 | 4/1996 |
| JP | 2002-301019 | 10/2002 |

* cited by examiner

*Primary Examiner* — John P Leubecker
(74) *Attorney, Agent, or Firm* — Scully, Scott, Murphy & Presser, P.C.

(57) ABSTRACT

An endoscope system, serving as a double-balloon endoscope system, includes an endoscope apparatus for examinations using an endoscope, a shape detection apparatus used in combination with the endoscope apparatus, and a balloon controller. The shape detection apparatus detects positions of respective points in an insertion section of the endoscope, estimates the shape of the insertion section on the basis of the detected positions, and displays an image representing the modeled shape of the insertion section corresponding to the estimated shape. The balloon controller controls balloons, serving as insertion support units, attached to the endoscope. The shape detection apparatus detects the states of the balloons controlled through the balloon controller and reflects the controlled states of the balloons on an image representing the shape of the insertion section. With this arrangement, the inflation/deflation states of the balloons and the insertion state can be visually confirmed in real time with ease.

13 Claims, 8 Drawing Sheets

DOUBLE-BALLOON ENDOSCOPE SYSTEM

CROSS REFERENCE TO RELATED APPLICATION

This application is a continuation application of PCT/JP2005/004807 filed on Mar. 17, 2005 and claims benefit of Japanese Application No. 2004-081650 filed in Japan on Mar. 19, 2004, the entire contents of which are incorporated herein by this reference.

BACKGROUND OF THE INVENTION

1. Field of the Invention

The present invention relates to a double-balloon endoscope system including an endoscope having a double balloon fixed to the outer surface of the distal end of an insertion section thereof.

2. Description of the Related Art

It is generally known that a gastrointestinal examination uses an endoscope having a flexible insertion section. In inserting the above-mentioned endoscope into deep part of the digestive tract, e.g., the small intestine, when the insertion section is inserted thereinto while being pushed, a force is hardly transmitted to the distal end of the insertion section because the intestine is complicatedly curved. It is, therefore, difficult to insert the insertion section into deep part.

For example, Japanese Unexamined Patent Application Publication No. 2002-301019 discloses a double-balloon endoscope apparatus including a double balloon that comprises two balloons disposed on the outer surfaces of the respective distal ends of an insertion section and an overtube through which the insertion section is inserted. The two balloons are alternately inflated and deflated so that at least one of the balloons is temporarily fixed to the intestine, so that the insertion section can be inserted into deep part.

In the insertion of the double-balloon endoscope apparatus into the small intestine, it is desirable that the shape of an endoscope be confirmed in order to grasp the state of insertion. It is recommended to perform an examination under X-ray fluoroscopy.

For instance, Japanese Unexamined Patent Application Publication No. 8-107875 discloses an endoscope-shape detection apparatus for detecting the shape of an endoscope, the apparatus including a magnetic-field generating element and a magnetic-field detecting element. In order to smoothly insert an insertion section of the endoscope into a curved body cavity, the apparatus detects the shape of the inserted endoscope using the magnetic-field generating element and the magnetic-field detecting element. The shape of the endoscope inserted into the body of a patient can be easily grasped.

SUMMARY OF THE INVENTION

The present invention provides a double-balloon endoscope system including:

an endoscope including a flexible insertion section to be inserted into a body cavity, a first device arranged in the insertion section, the first device including one of a magnetic-field generating element for generating a magnetic field and a magnetic-field detecting element for detecting a magnetic field, a fist balloon disposed on the outer surface of the distal end of the insertion section, a second balloon disposed on the outer surface of the distal end of an overtube unit through which the insertion section is inserted, and a second device arranged at a predetermined position in the overtube unit, the second device including the same element as that of the first device;

a third device arranged at a known position in the vicinity of a subject into which the insertion section is inserted, the third device including the other one of the magnetic-field generating element and the magnetic-field detecting element;

a balloon control unit for controlling the first and second balloons to inflate and/or deflate; and a state-image generating unit for processing a detection signal, obtained by detecting a magnetic field generated by the magnetic-field generating element through the magnetic-field detecting element, and detecting the inflation/deflation states of the balloons controlled through the balloon control unit to generate a state image representing the shape of the insertion section and the inflation state of at least one of the first and second balloons.

DETAILED DESCRIPTION OF THE PREFERRED EMBODIMENT(S)

An embodiment of the present invention will be described below with reference to the drawings.

First Embodiment

Structure

Figure 1:
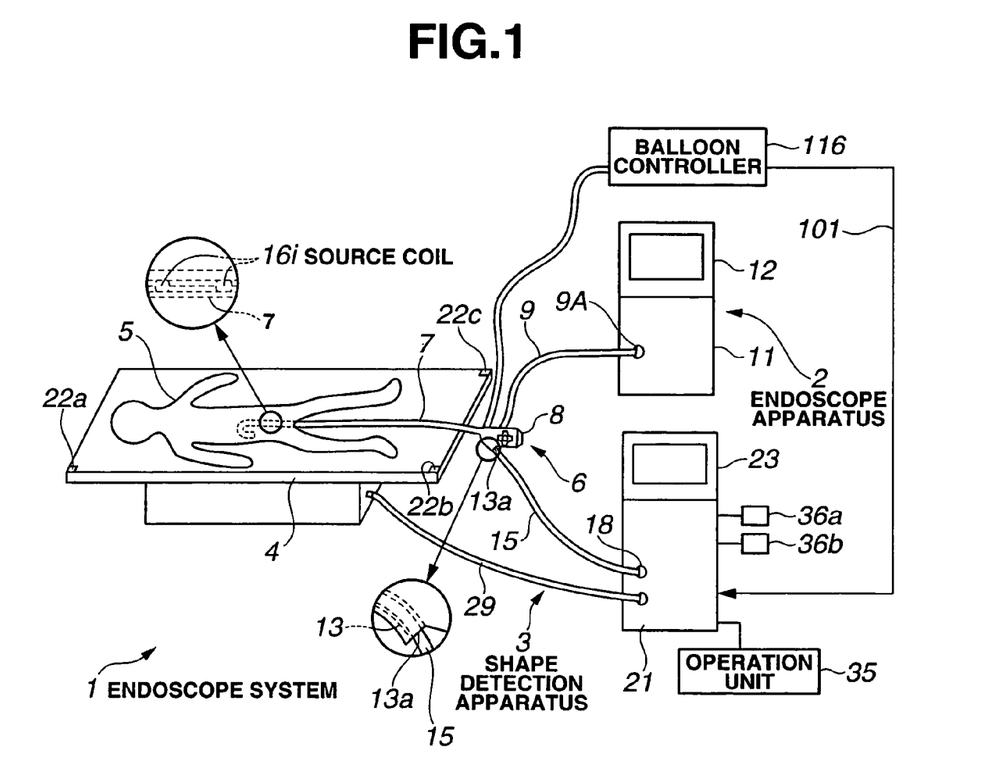
FIG. 1 is a diagram showing the structure of an endoscope system according to a first embodiment of the present invention.

Referring to FIG. 1, an endoscope system 1, serving as a double-balloon endoscope system according to the present embodiment, includes an endoscope apparatus 2 for examinations and the like using an endoscope 6, a shape detection apparatus 3, and a balloon controller 116. The shape detection apparatus 3, used in combination with the endoscope apparatus 2, detects the positions of respective points in an insertion section 7 of the endoscope 6 to estimate the shape of the insertion section 7 on the basis of the detected positions and displays an image of the modeled shape of the insertion section (the endoscope) corresponding to the estimated shape. The balloon controller 116 controls balloons, serving as insertion support units, attached to the endoscope. The shape detection apparatus 3 detects the states of the balloons controlled through the balloon controller 116 and reflects the controlled states of the balloons on the shape image of the insertion section.

A patient 5, serving as a subject, lies on a bed 4 (for endoscopy). The insertion section 7 of the endoscope 6 is inserted into the body cavity of the patient 5.

The endoscope 6 includes the insertion section 7 that is elongated and flexible, a large-diameter operation section 8 arranged at the back end of the insertion section 7, and a universal cable 9 extending from the side of the operation section 8. A connector 9A arranged at one end of the universal cable 9 is removably connected to a video processor 11.

A light guide (not shown) is inserted through the insertion section 7. The light guide extends through the universal cable 9 extending from the operation section 8, up to the connector 9A arranged at the end of the universal cable 9. Illumination light, emitted from a lamp of a light source (not shown) built in the video processor 11, is supplied to the end surface of the connector 9A. The light is transmitted through the light guide. The transmitted light is projected forward from the end surface of the distal end of the insertion section 7 attached to an illumination window (serving as illumination light projecting means).

An object, such as the interior wall of the body cavity or affected part, is illuminated with the illumination light projected from the illumination window. An objective lens (not shown) is attached to an observation window adjacent to the illumination window in the distal end. A CCD, as a solid-state image capturing device, is arranged at the focal plane of the objective lens. The CCD captures an image of the object.

When the CCD receives a CCD drive signal output from a CCD drive circuit in a signal processing unit (not shown) included in the video processor 11, an image signal obtained by photoelectric conversion (in the CCD) is read, the signal is transmitted through a signal line arranged in the insertion section 7 to the signal processing unit, the transmitted signal is processed and converted into a standard video signal, and the video signal is output to a color monitor 12. The color monitor 12 displays an endoscopic image in color, the image being formed on the photoelectric conversion plane of the CCD through the objective lens.

The operation section 8 includes a knob for bending. When the knob is rotated, a bendable portion in the vicinity of the distal end of the insertion section 7 can be bent. Accordingly, the distal end of the insertion section 7 is bent along a curved path in the body cavity so that the insertion section 7 is smoothly inserted into the body cavity.

The endoscope 6 has a hollow channel 13 formed in the insertion section 7. An accessory, such as forceps, is inserted into the channel 13 from an insertion inlet 13a at the proximal end of the channel 13. Consequently, the distal end of the accessory can be projected from a channel outlet at the distal end of the insertion section 7 for biopsy, therapy, or treatment.

A probe 15 for detection of the position and shape (of the insertion section 7 inserted into the body cavity) can be inserted into the channel 13 and the distal end of the probe 15 can be located at a predetermined position in the channel 13.

Figure 2:
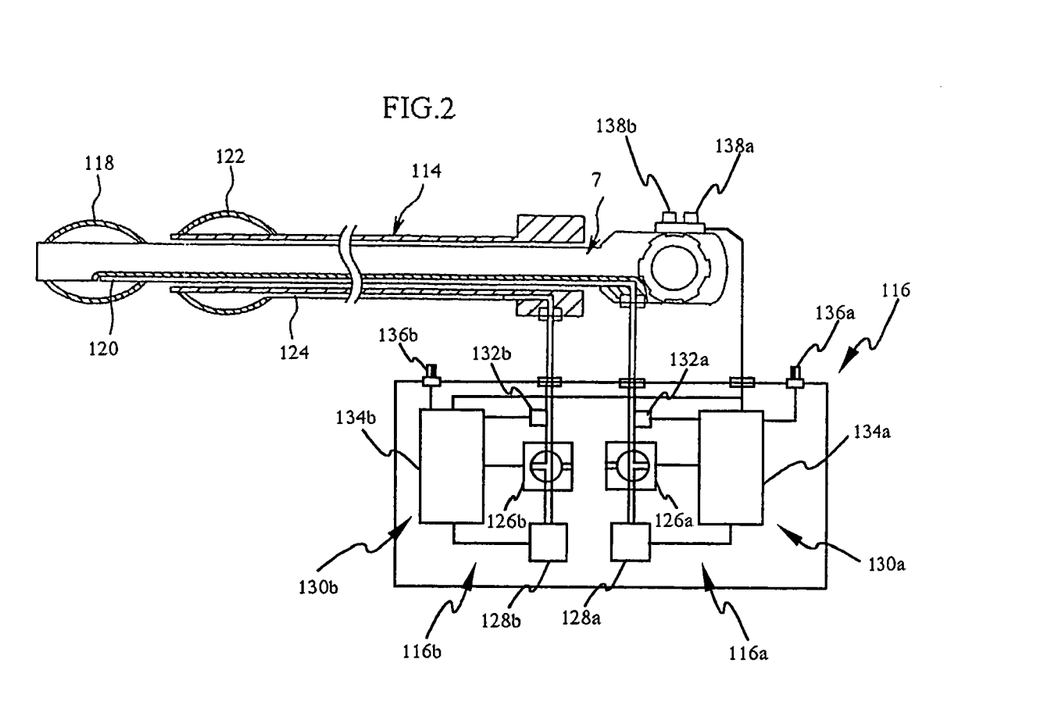
FIG. 2 is a diagram showing the structure of an endoscope and that of a balloon controller in FIG. 1.

As shown in FIG. 2, a balloon 118 for fixing the endoscope is attached to the outer surface of the distal end of the insertion section 7. An air supply tube 120 extends from the proximal end of the insertion section 7 up to the distal end thereof along the insertion section 7 and connects to the balloon 118 for fixing the endoscope.

An overtube 114, through which the insertion section 7 is inserted, is used for guiding during the insertion of the endoscope into the digestive tract. The overtube 114 has an inner diameter slightly larger than the outer diameter of the insertion section 7. The overtube 114 is flexible, similar to the insertion section 7.

In addition, a balloon 122 for fixing the overtube is attached to the outer surface of the distal end of the overtube 114. An air supply tube 124 extends from the proximal end of the overtube 114 to the distal end thereof and connects to the balloon 122 for fixing the overtube.

The balloon controller 116 includes pump units 116a and 116b. The pump unit 116a supplies air to the balloon 118 for fixing the endoscope. The other pump unit 116b supplies air to the balloon 122 for fixing the overtube.

The pump units 116a and 116b include pumps 128a and 128b and control units 130a and 130b, respectively. The pumps 128a and 128b are connected to the air supply tubes 120 and 124 via selector valves 126a and 126b, respectively.

The control units 130a and 130b measures the air pressures in the balloons 118 and 122 for fixing the endoscope and the overtube to control the pressures in the balloons, respectively. The control units 130a and 130b includes pressure sensors 132a and 132b and control boards 134a and 134b, respectively.

The pressure sensor 132a is disposed at a midpoint in a path between the pump 128a and the air supply tube 120. The pressure sensor 132b is disposed at a midpoint in a path between the pump 128b and the air supply tube 124. The pressure sensors 132a and 132b measure the pressures in the respective paths, so that the sensors can detect the air pressures in the balloons 118 and 122, respectively.

The pressure sensors 132a and 132b are connected to the control boards 134a and 134b, respectively. The pressure sensors 132a and 132b transmit the measurement results to the control boards 134a and 134b, respectively.

The pumps 128a and 128b and the selector valves 126a and 126b are connected to the control boards 134a and 134b, respectively. The control boards 134a and 134b control the ON/OFF operations of the pumps 128a and 128b and also control the air supply/exhaust operations of the selector valves 126a and 126b.

In addition, the control boards 134a and 134b control the respective pumps 128a and 128b on the basis of the measurement results obtained by the pressure sensors 132a and 132b so that the pressures in the respective balloons 118 and 122 are optimized.

The control boards 134a and 134b further include pressure control units 136a and 136b whereby the air pressures in the balloons 118 and 122 are manually controlled, respectively. Accordingly, the air pressures can be fine controlled in accordance with the condition of the digestive tract of the patient 5. Each of the pressure control units 136a and 136b can be realized by, e.g., a volume controller.

Remote switches 138a and 138b for control of the pump units 116a and 116b are disposed in the proximal end of the endoscope at a hand of an operator. The remote switches 138a and 138b are connected to the control boards 134a and 134b, respectively.

The operator, therefore, operates the remote switches 138a and 138b at hand, so that the respective balloons 118 and 122 can be inflated and/or deflated while the internal pressures of the balloons are optimally set.

Figure 3:
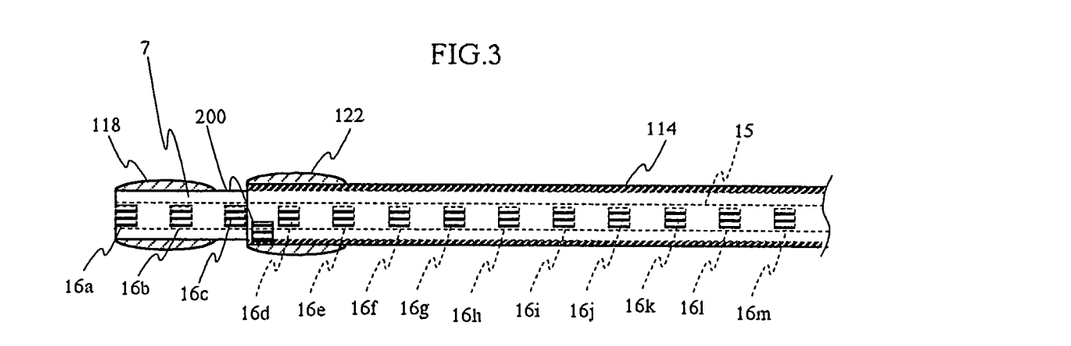
FIG. 3 is a diagram showing source coils arranged in the distal end of an overtube in FIG. 2.

Referring to FIG. 3, a source coil 200 is disposed in the distal end of the overtube 114. The source coil 200 serves as a magnetic-field generating element for generating a magnetic field.

Figure 4:
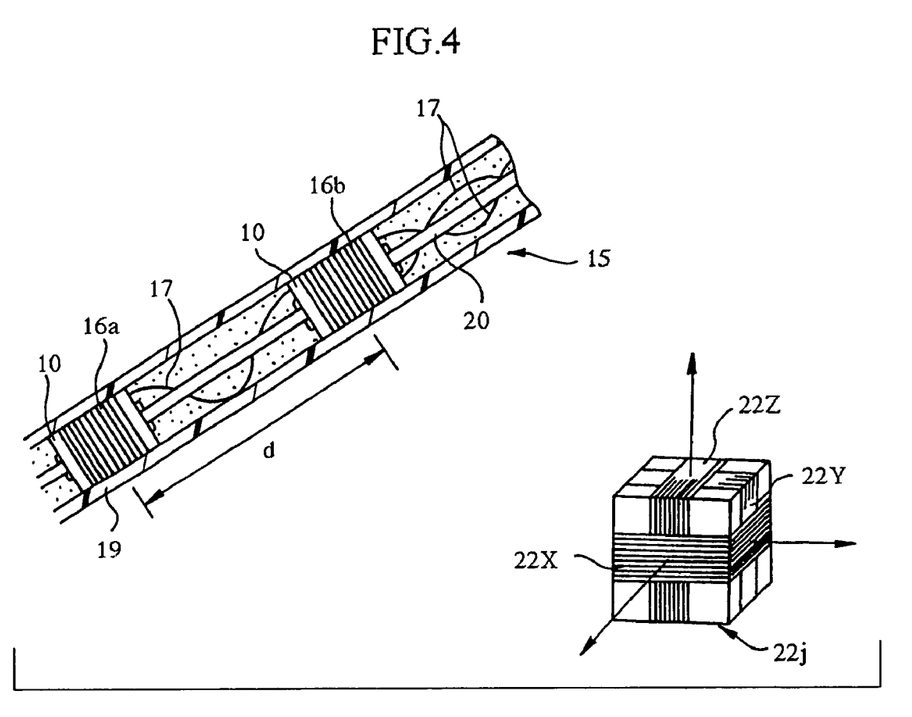
FIG. 4 includes a diagram showing a probe having the source coils in FIG. 1 and a diagram showing a triaxial sense coil.

Referring to FIG. 4, a plurality of source coils 16a, 16b, . . . (represented by reference numeral 16i), each serving as a magnetic-field generating element for generating a magnetic field, are arranged in the probe 15, which is inserted through the channel 13 of the endoscope 6. The source coils are arranged at, e.g., a predetermined pitch d in a flexible insulating tube 19 having a circular cross section. The source coils are fixed to a flexible support 20 and the inner surface of the tube 19 using an insulating adhesive.

Each source coil 16i includes a solenoid coil formed by winding an insulation-coated conductor around, e.g., a cylindrical rigid insulating core 10. A lead line connected to one end of each source coil 16i passes through the support 20. A lead line 17 connected to the other end of each source coil 16i passes through the tube 19 and extends up to the hand of the operator.

Similarly, the source coil 200 includes a solenoid coil formed by winding an insulation-coated conductor around, e.g., a cylindrical rigid insulating core although this is not shown in the figure.

The position of each source coil 16i is set to a known position in the insertion section 7 of the endoscope 6. When the position of each source coil 16i is detected, the discrete positions (specifically, the positions of the respective source coils 16i) of the insertion section 7 of the endoscope 6 and the position of the balloon 118 for fixing the endoscope can be detected.

Similarly, the position of the source coil 200 is set to a known position in the distal end of the overtube 114. When the position of the source coil 200 is detected, the relative position of the balloon 122 for fixing the overtube on the insertion section 7 of the endoscope 6 can be detected (see FIG. 3).

When those discrete positions are detected, the position of each part therebetween can be substantially estimated. Accordingly, the approximate shape of the insertion section 7 of the endoscope 6 inserted into the body cavity can be obtained by detecting the discrete positions. In addition, the relative positions of the balloons 118 and 122 for fixing the endoscope and the overtube can be detected on the insertion section 7 of the endoscope 6.

Again referring to FIG. 1, the lead lines 17, connected to the respective source coils 16i and the source coil 200, are connected to a connector 18 which is arranged at the back end of the probe 15 or a cable extending from the back end of the probe 15. The connector 18 is connected to a connector port of a main body 21 of the (endoscope-) shape detection apparatus. A drive signal is supplied to each of the source coils 16i and the source coil 200, thus generating magnetic fields used for position detection.

Triaxial sense coils 22a, 22b, and 22c (represented by 22j), serving as magnetic-field detecting elements, are attached to known positions of the bed 4, e.g., three corners thereof. Those triaxial sense coils 22j are connected to the main body 21 of the shape detection apparatus 3 via a cable 29 extending from the bed 4.

Referring to FIG. 4, each triaxial sense coil 22j includes three coil segments 22X, 22Y, and 22Z wound in three directions such that respective coil planes are orthogonal to each other. Each of the coil segments 22X, 22Y, and 22Z detects a signal proportional to the intensity of the magnetic field of an axial direction component orthogonal to the associated coil plane.

The main body 21 of the shape detection apparatus detects the positions of the source coils 16i and the source coil 200 on the basis of outputs of the triaxial sense coils 22j, estimates the shape of the insertion section 7 of the endoscope 6 inserted into the patient 5 and the relative positions of the balloons 118 and 122 for fixing the endoscope and the overtube, and displays a C.G (computer graphics) image corresponding to the estimated shape and balloons on a monitor 23.

Inflation/deflation state information regarding the states (inflation/deflation states) of the balloons 118 and 122 for fixing the endoscope and the overtube is output from the balloon controller 116 to the main body 21 of the shape detection apparatus via a signal cable 101.

The detailed structure of the main body 21 of the shape detection apparatus and the principle and algorithm for estimating the shape of the insertion section 7 of the endoscope 6 through the main body 21 of the shape detection apparatus are disclosed in detail in, e.g., Japanese Unexamined Patent Application Publication No. 8-107875 and are known. Accordingly, a description thereof is omitted.

Operation

The outline of the operation of inserting (the insertion section 7 of) the endoscope 6 using the balloons 118 and 122 for fixing the endoscope and the overtube controlled through the balloon controller 116 will now be described with reference to FIGS. 5 to 11.

Figure 5:
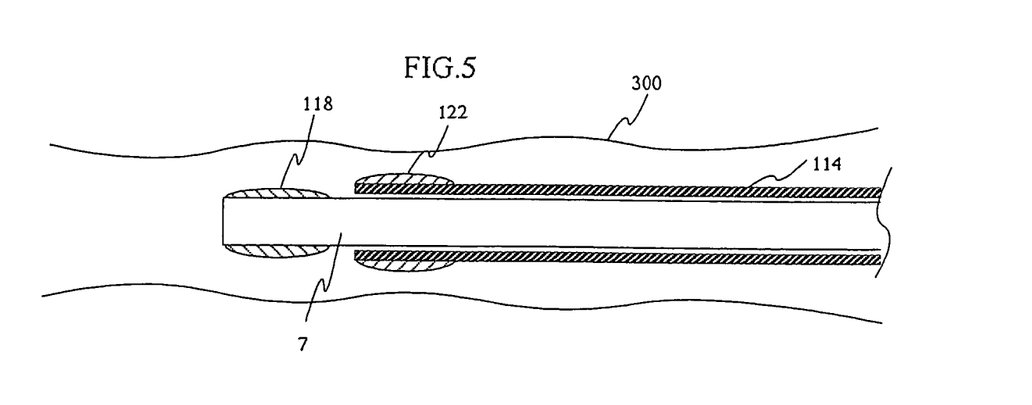
FIG. 5 is a first diagram showing the operation of inserting an insertion section of the endoscope having a balloon for fixing the endoscope and a balloon for fixing the overtube in FIG. 2.

Referring to FIG. 5, the insertion section 7 is inserted into the overtube 114 under the condition that air is exhausted from the balloons 118 and 122 to deflate the balloons. Under this condition, inserting the endoscope 6 into the patient 5 is started.

Figure 6:
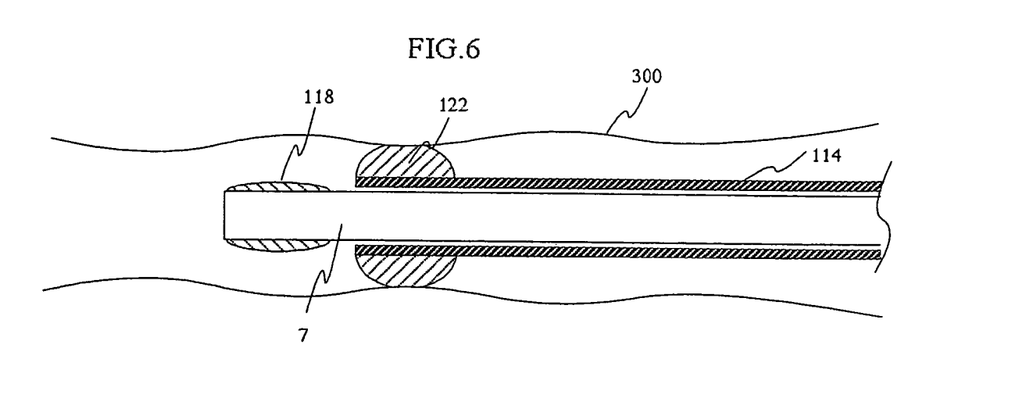
FIG. 6 is a second diagram showing the operation of inserting the insertion section of the endoscope having the balloon for fixing the endoscope and the balloon for fixing the overtube in FIG. 2.

Subsequently, the distal end of the insertion section 7 and that of the overtube 114 are inserted up to, e.g., the descending part of the duodenum. At that time, as shown in FIG. 6, the remote switch 138b is operated to supply air from the pump 128b to the balloon 122 for fixing the overtube attached in the distal end of the overtube 114, thus inflating the balloon 122. Consequently, the overtube 114 is fixed to the intestinal canal 300.

Figure 7:
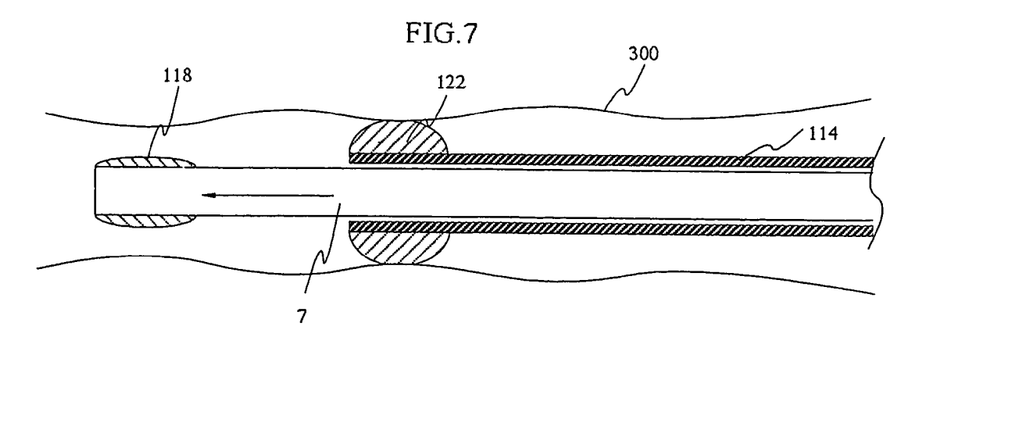
FIG. 7 is a third diagram showing the operation of inserting the insertion section of the endoscope having the balloon for fixing the endoscope and the balloon for fixing the overtube in FIG. 2.

Under the condition that the insertion section 7 is made as straight as possible, the insertion section 7 alone is inserted into deep part as shown in FIG. 7 while the inflation state of the balloon 122 for fixing the overtube on the overtube 114 is kept.

Figure 8:
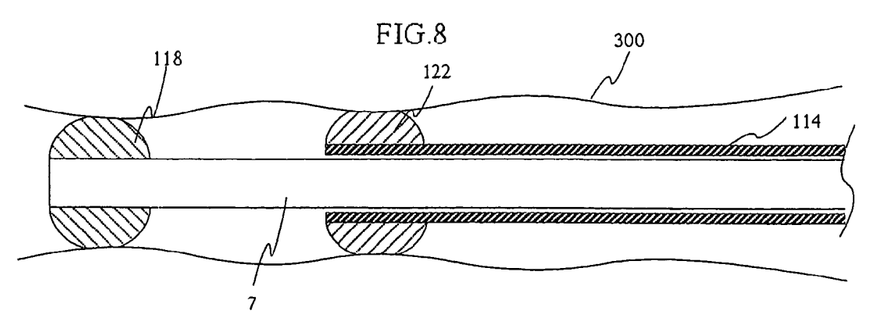
FIG. 8 is a fourth diagram showing the operation of inserting the insertion section of the endoscope having the balloon for fixing the endoscope and the balloon for fixing the overtube in FIG. 2.

After the insertion section 7 is inserted by a predetermined distance, the remote switch 138a is operated to supply air from the pump 128a to the balloon 118 for fixing the endoscope attached in the distal end of the insertion section 7, thus inflating the balloon 118 as shown in FIG. 8. Consequently, the balloon 118 for fixing the endoscope is fixed to the intestinal canal 300.

Figure 9:
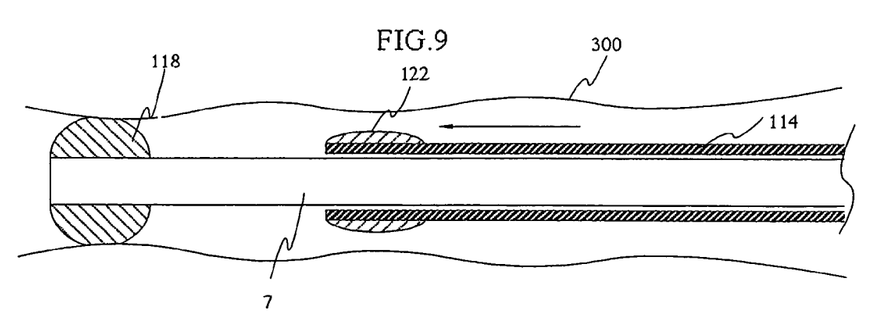
FIG. 9 is a fifth diagram showing the operation of inserting the insertion section of the endoscope having the balloon for fixing the endoscope and the balloon for fixing the overtube in FIG. 2.

As shown in FIG. 9, the remote switch 138b is operated to exhaust air from the balloon 122 for fixing the overtube through the selector valve 126b, thus deflating the balloon 122 for fixing the overtube.

Figure 10:
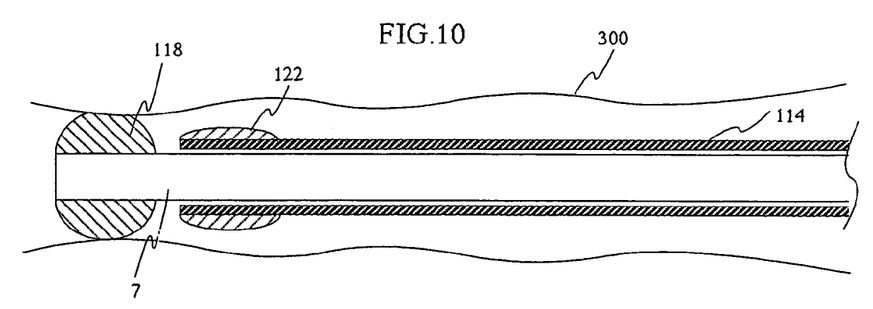
FIG. 10 is a sixth diagram showing the operation of inserting the insertion section of the endoscope having the balloon for fixing the endoscope and the balloon for fixing the overtube in FIG. 2.

Referring to FIG. 10, the overtube 114 is inserted into the deep part along the insertion section 7, so that the distal end of the overtube 114 is located in the vicinity of the distal end of the insertion section 7.

Figure 11:
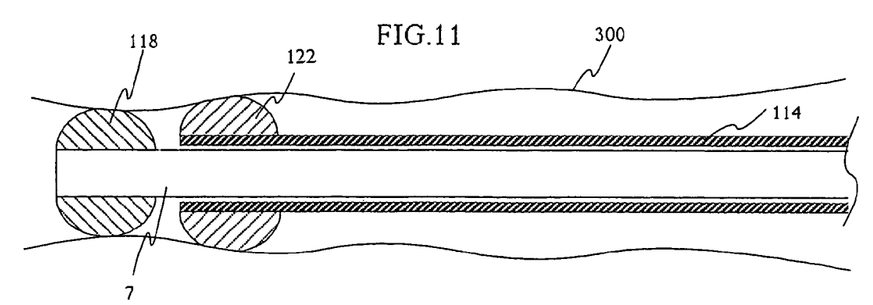
FIG. 11 is a seventh diagram showing the operation of inserting the insertion section of the endoscope having the balloon for fixing the endoscope and the balloon for fixing the overtube in FIG. 2.

As shown in FIG. 11, under the condition that the distal end of the overtube 114 is located in the vicinity of the distal end of the insertion section 7, the remote switch 138b is operated to inflate the balloon 122 for fixing the overtube, thus fixing the overtube 114 to the intestinal wall. In addition, the remote switch 138a is operated to open the selector valve 126a, thus deflating the balloon 118 for fixing the endoscope such that the state in FIG. 6 is obtained. Operation steps shown in FIGS. 6 to 11 are repeated to insert the insertion section 7 into deeper part.

According to the present embodiment, the shape of the insertion section 7 of the endoscope 6 inserted into the patient 5 and the relative positions of the balloons 118 and 122 for fixing the endoscope and the overtube are estimated. A C. G (computer graphics) image corresponding to the estimated shape and balloons at the relative positions based on the inflation/deflation state information is displayed on the monitor 23. Advantageously, the above-described insertion operation can be performed while the operation is observed on the monitor 23 in real time.

Figure 12:
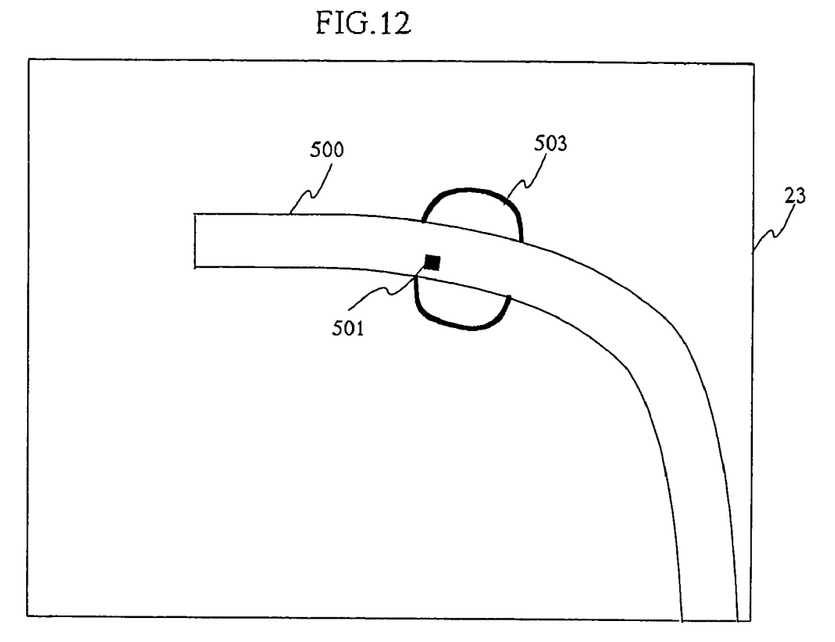
FIG. 12 is a first diagram showing the shape of the inserted insertion section and the inflation states of the balloon for fixing the endoscope and the balloon for fixing the overtube displayed on a monitor of a shape detection apparatus in FIG. 1.

Specifically, as shown in FIG. 12, a shape image 500 of the inserted insertion section 7 is displayed on the monitor 23. A coil marker 501 is also displayed at a position corresponding to the source coil 200 provided for the overtube 114 on the shape image 500. In addition, the relative positions of the balloons 118 and 122 for fixing the endoscope and the overtube are estimated. On the basis of the estimated positions, a marker 502 for endoscope fixing balloon is displayed at a position corresponding to the balloon 118 for fixing the endoscope and a marker 503 for overtube fixing balloon is displayed at a position corresponding to the balloon 122 for fixing the overtube on the shape image 500 of the insertion section 7.

In this case, on the basis of the inflation/deflation state information, each of the markers 502 and 503 for endoscope fixing balloon and overtube fixing balloon is displayed so long as the corresponding balloon is inflated (in the inflation state). Advantageously, the fixed state using the balloon can be visually confirmed with ease. The distal end of the overtube 114 with the deflated balloon for fixing the overtube (in the deflation state), i.e., the position of the balloon for fixing the overtube can be visually confirmed on the basis of the coil marker 501.

Figure 13:
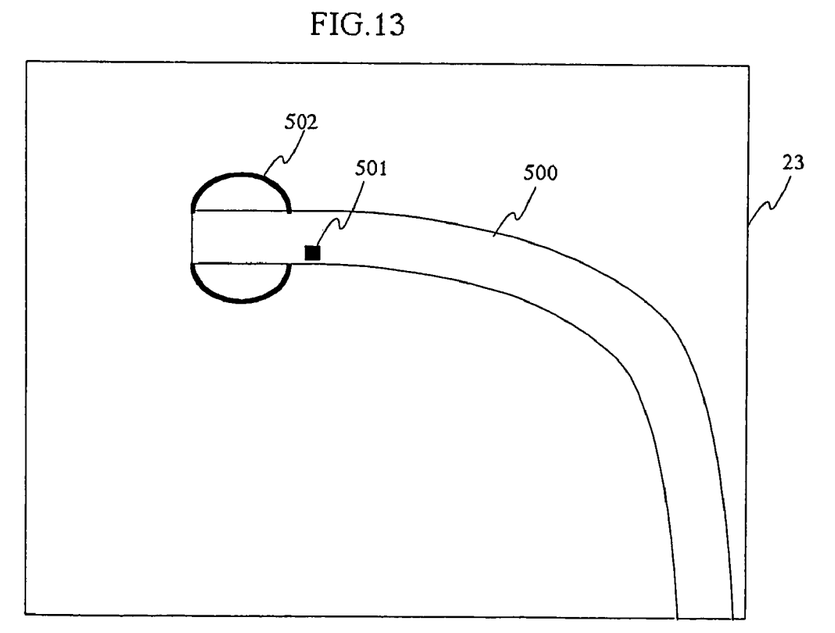
FIG. 13 is a second diagram showing the shape of the inserted insertion section and the inflation states of the balloon for fixing the endoscope and the balloon for fixing the overtube displayed on the monitor of the shape detection apparatus in FIG. 1.
Figure 14:
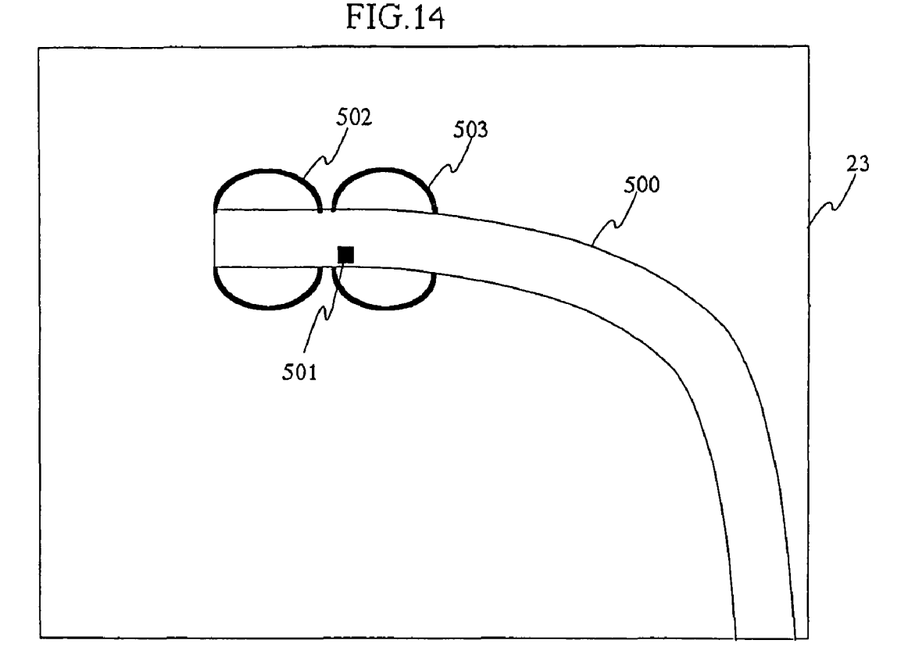
FIG. 14 is a third diagram showing the shape of the inserted insertion section and the inflation states of the balloon for fixing the endoscope and the balloon for fixing the overtube displayed on the monitor of the shape detection apparatus in FIG. 1.

FIG. 12 shows an example of the shape displayed on the monitor 23, the example corresponding to the above-described insertion operation shown in FIG. 7. FIG. 13 shows an example of the shape displayed on the monitor 23, the example corresponding to the insertion operation shown in FIG. 10. FIG. 14 shows an example of the shape displayed on the monitor 23, the example corresponding to the insertion operation shown in FIG. 11.

Advantages

The markers 502 and 503 for endoscope fixing balloon and overtube fixing balloon representing the inflation states of the balloons 118 and 122 for fixing the endoscope and the overtube are displayed superimposed on the shape image 500, so that the fixed state using the balloon 118 or 112 and the shape of the inserted insertion section 7 can be visually confirmed in real time at a glance. Advantageously, the operation of inserting the endoscope 6 can be easily performed with reliability, leading to a reduction in burden of the operator and a reduction in examination time. The patient 5 can be examined with little pain.

Figure 15:
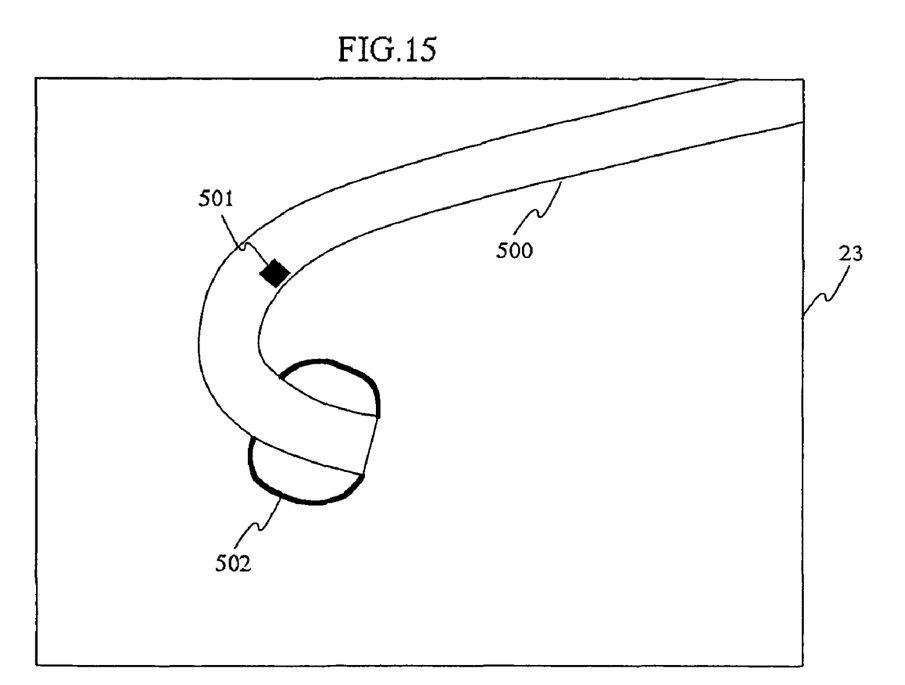
FIG. 15 is a fourth diagram showing the shape of the inserted insertion section and the inflation states of the balloon for fixing the endoscope and the balloon for fixing the overtube displayed on the monitor of the shape detection apparatus in FIG. 1.

Assuming that the insertion section 7 is inserted into, e.g., the curved intestinal canal while the insertion section 7 is curved, when the overtube 114 is inserted into deep part along the insertion section 7, the insertion operation puts a load on the overtube 114 in the curved part of the insertion section 7. Disadvantageously, it will cause difficulty in the insertion operation. According to the present embodiment, the shape of the endoscope is displayed on the monitor 23 as shown in FIG. 15. Simultaneously, the coil marker 501, corresponding to the source coil 200, representing the position of the balloon 122 for fixing the overtube is displayed. Advantageously, the insertion state can be visually confirmed with ease. For instance, when the intestinal canal is straightened using the insertion section 7 so that the insertion operation is not affected, the overtube 114 can be easily inserted.

Figure 16:
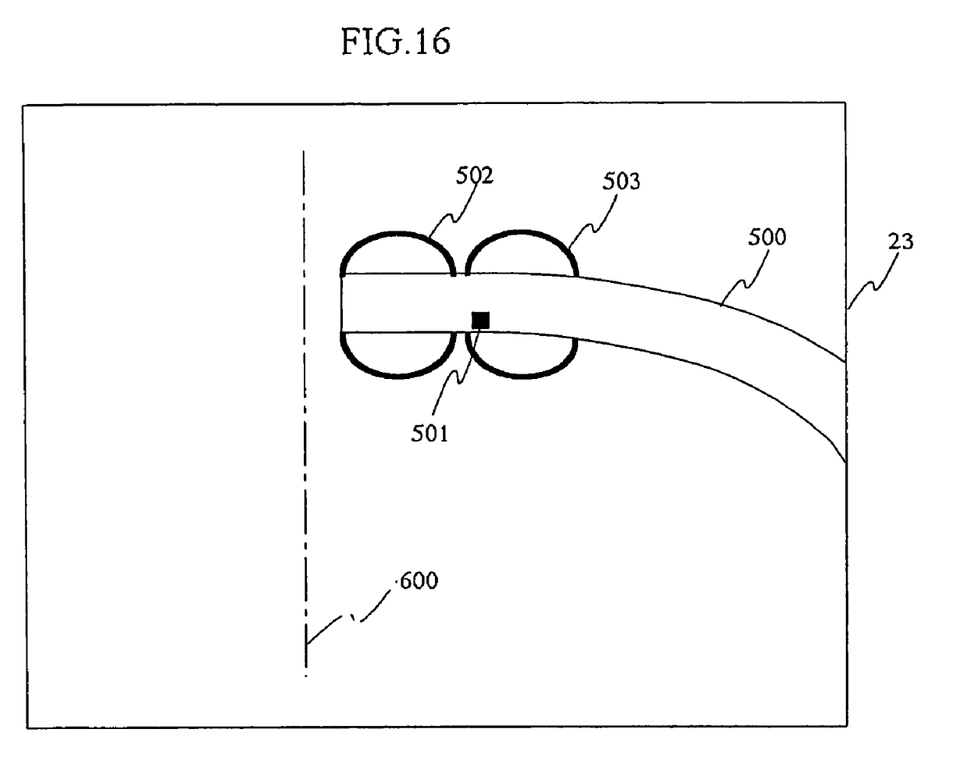
FIG. 16 is a fifth diagram showing the shape of the inserted insertion section and the inflation states of the balloon for fixing the endoscope and the balloon for fixing the overtube displayed on the monitor of the shape detection apparatus in FIG. 1.

During the insertion of the insertion section 7 of the endoscope 6 into the intestinal canal, in order to, e.g., shorten the intestinal canal, the balloons are drawn while the inflation states are being held. In other words, the insertion operation is performed in such a manner that the insertion section 7 is moved forward and backward while the balloons 118 and 122 for fixing the endoscope and the overtube are inflated and/or deflated. The forward and backward movement of the insertion section 7 in the intestinal canal may make the position of the inserted insertion section 7 in the intestinal canal unclear. According to the present embodiment, e.g., the previous insertion depth of the distal end of the insertion section 7 can be designated by operating an operation unit 35 (see FIG. 1). When the previous insertion depth of the distal end of the insertion section 7 is designated, a reference-position line marker 600 is displayed superimposed on the monitor 23 as shown in FIG. 16. Advantageously, the insertion section 7 can be easily inserted into deep part of, e.g., the intestinal canal.

According to the present embodiment, as described above, the insertion state of the endoscope can be visually confirmed even if the insertion is not performed under X-ray fluoroscopy. Advantageously, the endoscope can be easily inserted into deep part, such as the intestinal canal, of a patient without X-ray exposure. Unfortunately, since images of the balloons are not captured under X-ray fluoroscopy, the positions and inflation/deflation states of the balloons cannot be grasped. According to the present embodiment, the markers 502 and 503 for endoscope fixing balloon and overtube fixing balloon based on the inflation/deflation state information and the coil marker 501 representing the source coil 200 can be displayed. Advantageously, the positions and inflation/deflation states of the balloons can be easily grasped in real time.

In the arrangement according to the present embodiment, the source coil 200 is disposed in the distal end of the overtube 114. The position of the balloon for fixing the overtube can be visually confirmed with ease on the shape image of the inserted insertion section 7 because the coil marker 501 corresponding to the source coil 200 is displayed. The present invention is not limited to the above arrangement. When the source coil 200 is disposed at a predetermined position on the overtube 114, the position of the balloon for fixing the overtube can be calculated by arithmetic operation. In this case, a balloon marker is displayed at the calculated position instead of the coil marker 501. Advantageously, even when the balloon for fixing the overtube is deflated and the marker 503 for overtube fixing balloon is not displayed, the position of the balloon for fixing the overtube can be visually confirmed with ease.

The present invention is not limited to the foregoing embodiment but many modifications and variations are possible without departing from the spirit and scope of the present invention.

What is claimed is:

1. A double-balloon endoscope system comprising:
   an endoscope including a flexible insertion section to be inserted into a body cavity, a first device arranged in the insertion section, the first device including one of a magnetic-field generating element for generating a magnetic field and a magnetic-field detecting element for detecting a magnetic field, a first balloon disposed on the outer surface of the distal end of the insertion section, a second balloon disposed on the outer surface of the distal end of an overtube unit through which the insertion section is inserted, and a second device arranged at a predetermined position in the overtube unit, the second device including the same element as that of the first device;
   a third device arranged at a known position in the vicinity of a subject into which the insertion section is inserted, the third device including the other one of the magnetic-field generating element and the magnetic-field detecting element;
   a balloon control unit for controlling the first and second balloons to inflate and/or deflate; and
   a state-image generating unit for processing a detection signal, obtained by detecting a magnetic field generated by the magnetic-field generating element through the magnetic-field detecting element, and detecting the inflation/deflation states of the balloons controlled through the balloon control unit to generate a state image representing the shape of the insertion section and the inflation state of at least one of the first and second balloons.

2. The double-balloon endoscope system according to claim 1, wherein
   the first device includes at least one first source coil for generating a magnetic field, the second device includes a second source coil for generating a magnetic field, and the third device includes a sense coil for detecting the magnetic fields generated from the at least one first source coil and the second source coil, and
   the state-image generating unit drives the at least one first source coil and the second source coil, processes the detection signals detected through the sense coil, and detects the inflation/deflation states controlled through the balloon control unit to generate the state image.

3. The double-balloon endoscope system according to claim 2, wherein the at least one first source coil includes a group of source coils arranged along the insertion axis of the insertion section.

4. The double-balloon endoscope system according to claim 3, wherein the state-image generating unit superimposes a balloon position marker indicating the position of the second balloon on the state image.

5. The double-balloon endoscope system according to claim 4, wherein the state-image generating unit calculates the position of the second balloon on the basis of the magnetic field, generated from the second source coil, detected through the magnetic-field detecting element.

6. The double-balloon endoscope system according to claim 5, wherein the state-image generating unit designates the position of the distal end of the insertion section and superimposes a distal-end position marker indicating the position of the distal end on the state image.

7. The double-balloon endoscope system according to claim 4, wherein the state-image generating unit designates the position of the distal end of the insertion section and superimposes a distal-end position marker indicating the position of the distal end on the state image.

8. The double-balloon endoscope system according to claim 3, wherein the state-image generating unit designates the position of the distal end of the insertion section and superimposes a distal-end position marker indicating the position of the distal end on the state image.

9. The double-balloon endoscope system according to claim 2, wherein the state-image generating unit superimposes a balloon position marker indicating the position of the second balloon on the state image.

10. The double-balloon endoscope system according to claim 9, wherein the state-image generating unit calculates the position of the second balloon on the basis of the magnetic field, generated from the second source coil, detected through the magnetic-field detecting element.

11. The double-balloon endoscope system according to claim 10, wherein the state-image generating unit designates the position of the distal end of the insertion section and superimposes a distal-end position marker indicating the position of the distal end on the state image.

12. The double-balloon endoscope system according to claim 9, wherein the state-image generating unit designates the position of the distal end of the insertion section and superimposes a distal-end position marker indicating the position of the distal end on the state image.

13. The double-balloon endoscope system according to claim 2, wherein the state-image generating unit designates the position of the distal end of the insertion section and superimposes a distal-end position marker indicating the position of the distal end on the state image.

* * * * *